(12) United States Patent
Purdy et al.

(10) Patent No.: US 8,211,168 B2
(45) Date of Patent: Jul. 3, 2012

(54) GRAFT MATERIAL, STENT GRAFT AND METHOD

(75) Inventors: James D. Purdy, Lafayette, IN (US); David D. Grewe, West Lafayette, IN (US); Kurt Dierking, Brookston, IN (US); Lal Ninan, Santa Rosa, CA (US); Jichao Sun, West Lafayette, IN (US)

(73) Assignees: Cook Biotech Incorporated, West Lafayette, IN (US); Cook Medical Technologies LLC, Bloomington, IN (US)

( * ) Notice: Subject to any disclaimer, the term of this patent is extended or adjusted under 35 U.S.C. 154(b) by 740 days.

(21) Appl. No.: 11/708,412

(22) Filed: Feb. 20, 2007

(65) Prior Publication Data
US 2007/0237973 A1 Oct. 11, 2007

Related U.S. Application Data

(60) Provisional application No. 60/775,509, filed on Feb. 21, 2006.

(51) Int. Cl.
*A61F 2/06* (2006.01)
*A61F 2/02* (2006.01)

(52) U.S. Cl. ........ 623/1.44; 623/1.13; 623/1.39; 623/1.46; 623/1.47; 623/1.48; 623/23.72; 623/23.75; 623/23.76

(58) Field of Classification Search ........ 623/1.38–1.39, 623/1.42–1.48, 1.13, 1.4–1.41, 23.72–23.76
See application file for complete search history.

(56) References Cited

U.S. PATENT DOCUMENTS

| 3,772,137 | A | | 11/1973 | Tolliver |
| 4,473,665 | A | | 9/1984 | Martini-Vvedensky et al. |
| 4,604,762 | A | * | 8/1986 | Robinson ............ 623/1.44 |
| 4,675,361 | A | | 6/1987 | Ward, Jr. |
| 4,861,830 | A | | 8/1989 | Ward, Jr. |
| 4,902,508 | A | | 2/1990 | Badylak et al. |
| 4,956,178 | A | | 9/1990 | Badylak et al. |

(Continued)

FOREIGN PATENT DOCUMENTS
WO WO 02/15951 2/2002
(Continued)

OTHER PUBLICATIONS

C. Heeschen et al., "Nicotine stimulates angiogenesis and promotes tumor growth and atherosclerosis," *Nature Medicine*, 7(7):833-839 (2001).

(Continued)

*Primary Examiner* — Paul Prebilic
*Assistant Examiner* — Andrew Iwamaye
(74) *Attorney, Agent, or Firm* — Brinks Hofer Gilson & Lione (57) ABSTRACT

This invention is directed to graft materials for implanting, transplanting, replacing, or repairing a part of a patient and to methods of making the graft materials. The present invention is also directed to stent grafts and endoluminal prostheses formed of the graft materials. More specifically, the present invention is a graft material which includes porous polymeric sheet, extracellular matrix material (ECM) disposed on at least a portion of the porous polymeric sheet and at least one polymer layer disposed on at least a portion of the ECM. The ECM may be in a gel form. The polymeric sheet and the polymer layer may be made from foam material and may comprise a polyurethane urea and a surface modifying agent such as siloxane.

19 Claims, 4 Drawing Sheets

U.S. PATENT DOCUMENTS

| | | | |
|---|---|---|---|
| 5,017,664 A | 5/1991 | Grasel et al. | |
| 5,037,377 A | 8/1991 | Alonso | |
| 5,160,674 A | 11/1992 | Colton et al. | |
| 5,275,826 A | 1/1994 | Badylak et al. | |
| 5,354,329 A * | 10/1994 | Whalen | 623/1.44 |
| 5,516,533 A | 5/1996 | Badylak et al. | |
| 5,589,563 A | 12/1996 | Ward et al. | |
| 5,609,629 A * | 3/1997 | Fearnot et al. | 623/1.42 |
| 5,693,085 A * | 12/1997 | Buirge et al. | 623/1.13 |
| 6,206,931 B1 * | 3/2001 | Cook et al. | 623/23.75 |
| 6,264,992 B1 | 7/2001 | Voytik-Harbin et al. | |
| 6,440,166 B1 * | 8/2002 | Kolluri | 623/1.4 |
| 6,514,283 B2 * | 2/2003 | DiMatteo et al. | 623/1.13 |
| 6,638,312 B2 * | 10/2003 | Plouhar et al. | 623/23.72 |
| 6,656,215 B1 * | 12/2003 | Yanez et al. | 623/1.13 |
| 6,702,848 B1 | 3/2004 | Zilla et al. | |
| 6,702,849 B1 | 3/2004 | Dutta et al. | |
| 6,752,826 B2 * | 6/2004 | Holloway et al. | 623/1.13 |
| 7,160,318 B2 | 1/2007 | Greenberg et al. | |
| 7,175,652 B2 | 2/2007 | Cook et al. | |
| 7,244,271 B2 * | 7/2007 | Lentz et al. | 623/1.44 |
| 2002/0065552 A1 * | 5/2002 | Jayaraman et al. | 623/1.46 |
| 2002/0187288 A1 | 12/2002 | Lim et al. | |
| 2003/0023316 A1 * | 1/2003 | Brown et al. | 623/23.72 |
| 2003/0143315 A1 | 7/2003 | Pui et al. | |
| 2003/0149471 A1 | 8/2003 | Briana et al. | |
| 2003/0229393 A1 * | 12/2003 | Kutryk et al. | 623/1.46 |
| 2004/0051201 A1 | 3/2004 | Greenhalgh et al. | |
| 2004/0082989 A1 * | 4/2004 | Cook et al. | 623/1.13 |
| 2005/0107868 A1 * | 5/2005 | Nakayama et al. | 623/1.39 |
| 2005/0220848 A1 * | 10/2005 | Bates | 424/443 |
| 2005/0273155 A1 | 12/2005 | Bahler et al. | |

FOREIGN PATENT DOCUMENTS

| | | |
|---|---|---|
| WO | WO 2005/112821 | 12/2005 |
| WO | WO 2005/115275 | 12/2005 |

OTHER PUBLICATIONS

C. Johnson et al., "Matrix Metalloproteinase-9 Is Required for Adequate Angiogenic Revascularization of Ischemic Tissues, Potential Role in Capillary Branching," *Circulation Research*, 94(2):262-268 (2004).

International Search Report for PCT Application No. PCT/US2007/004565 dated Jul. 2, 2008.

* cited by examiner

GRAFT MATERIAL, STENT GRAFT AND METHOD

RELATED APPLICATIONS

The present patent document claims the benefit of the filing date under 35 U.S.C. §119(e) of Provisional U.S. Patent Application Ser. No. 60/775,509, filed Feb. 21, 2006, which is hereby incorporated by reference.

TECHNICAL FIELD

This invention is directed to graft materials for implanting, transplanting, replacing, or repairing a part of a patient and to methods of making the graft materials. The present invention is also directed to endoluminal prostheses formed of the graft materials.

BACKGROUND

Identification of materials suitable for grafts can be difficult, because such materials must possess disparate properties. For example, vascular graft materials should exhibit mechanical stability under continuous stress, should have compliance similar to that of the host tissue, and should be nonthromogenic. In some applications, graft materials may also provide for endothelialization and have sufficient porosity to allow for capillarization. Other preferred properties of graft materials include being non-allergenic and non-carcinogenic. While all of these properties may be specifically designed into a material, it is also desirable for the material to be inexpensive to fabricate.

Portions of the human vasculature may be replaced or treated with synthetic vascular grafts. One typical area of application includes the replacement or treatment of blood vessels with vascular grafts. Synthetic vascular grafts may have wide variety of configurations and may be formed from a wide variety of materials. Conventional vascular graft implants include those which are formed from a biologically compatible material which retains an open lumen to permit blood to flow through the synthetic graft after implant. Polymeric structures typically used for vascular graft and stent procedures may include woven and non-woven textiles and other porous polymer sheets.

Graft materials comprising polymeric sheet comprising holes (porous polymeric sheet) and extracellular matrix material (ECM) disposed in the holes of the polymeric sheet, medical prostheses that include such graft materials, and methods of making and using them were previously described in U.S. patent application Ser. No. 11/093,759, which is incorporated herein by reference in its entirety.

SUMMARY

In one another embodiment, the invention is a graft material. The graft material includes a porous polymeric sheet, an extracellular matrix material (ECM) disposed on at least a portion of the polymeric sheet, and at least one polymer layer disposed on at least a portion of the ECM. The polymer layer may be disposed on the entire ECM. The polymeric sheet may include holes and the ECM layer extends into the holes. The polymer layer and the polymeric sheet may include a polyetherurethane urea and a surface modifying agent, such as siloxane. The polymeric sheet may be in the form of a foam. The ECM may be small intestine submucosa. The small intestine submucosa may be comminuted. The small intestine submucosa may be in a gel form. The polymeric sheet layer of the graft material may have disposed thereon one or more pairs of a further ECM layer and a further polymer layer.

In another embodiment, the invention is an endoluminal prosthesis. The endoluminal prosthesis includes a tubular graft material comprising a porous polymeric sheet, ECM disposed on at least a portion of the porous polymeric sheet, and at least one polymer layer disposed on at least a portion of the ECM. The endoluminal prosthesis further includes a stent disposed about the graft material. The stent may be a self-expanding stent or a balloon expandable stent. The ECM may be small intestine submucosa. The polymer layer may include a polyetherurethane urea and a surface modifying agent, such as siloxane. The polymer layer may be disposed on the entire ECM. The polymeric sheet may have holes and the ECM layer may extend into the holes.

In a further embodiment, the present invention is a method of making a graft material for implantation. The method includes providing a porous polymeric sheet, providing ECM, disposing ECM on at least a portion of the porous polymeric sheet, and disposing at least one polymer layer on at least a portion of the ECM. The ECM remains disposed on the porous polymeric sheet until after implantation.

DETAILED DESCRIPTION

Unless defined otherwise, all technical and scientific terms used herein have the same meaning as commonly understood to one of ordinary skill in the art to which this invention belongs.

The term "graft" means any replacement for a bodily tissue or for a function of the bodily tissue. A graft may be transplanted from a donor to a recipient to repair a part of a body, and in some cases the patient can be both donor and recipient. For example, a graft may replace tissue that has been destroyed or create new tissue where none exists.

The term "sheet" means a monolithic layer of material. As used herein, the term "sheet" does not imply any particular shape, but includes flat layers, tubes, or other thin shaped objects. As used herein, the term "sheet" specifically includes materials formed from individual fibers, such as knitted or woven textiles or nonwoven textiles as well as extruded, sprayed, cast, and dipped materials and porous polymers. The term "polymeric sheet" means a monolytic layer of textile or other porous polymer material, formed from, for example, polyesters, fluorinated polymers, polysiloxanes, polyurethanes, polyolefins, polyacrylonitrile, nylons, polyaramids and polysulfones. The term "porous sheet" means a cohesive layer of material containing holes, such as small interstices or pores.

The term "holes" means spaces that intervene between parts of the polymeric sheet. Holes include interstices, pores, cavities, apertures, and spaces. For example, holes may be between fibers of the textile material, holes may be on a fiber of the textile material as well as the space surrounding fibers in a non-woven material; or pores in a foamed material.

The term "tissue" refers to an aggregation of similarly specialized cells united in the performance of a particular function. The term "tissue" encompass all types of biological tissue, including both hard and soft tissue, connective tissue (e.g., hard forms such as osseous tissue or bone), as well as other muscular or skeletal tissue.

The term "filament" refers to a long fiber. In this specification, it generally refers to a long, single fiber of the textile. The term filament or fiber encompasses fibers, yarns, threads, filaments and the like.

The terms "biodegradable" and "bioerodible" refers to something, such graft material, implant, coating, or dressing, that when placed the in vivo environment of its intended use will eventually dissolute into constituent parts that may be metabolized or excreted, under the conditions normally present in a living tissue. In exemplary embodiments, the rate and/or extent of biodegradation or bioerosion may be controlled in a predictable manner.

The term "endoluminal" refers to or describes objects that can be placed inside a lumen in a human or animal body. A lumen can be an existing lumen or a lumen created by surgical intervention. This includes lumens such as blood vessels, parts of the gastrointestinal tract, ducts such as bile ducts, parts of the respiratory system, etc. "Endoluminal device" or "endoluminal prosthesis" thus describes devices that can be placed inside one of these lumens.

The term "tubular" refers to the general shape of an endoluminal device which allows the device to carry fluid along a distance or fit within a tubular structure such as an artery. Tubular prosthetic devices include both branched and bifurcated devices.

The term "stent" refers to any device or structure that adds rigidity, expansion force or support to a prosthesis.

The term "stent graft" refers to a type of endoluminal prosthesis made of a tubular graft material and supported by at least one stent.

The term "healing" means replacing, repairing, healing, or treating of damaged or diseased tissues of a patient's body.

The terms "patient," "subject," and "recipient" as used in this application refer to any mammal, especially humans.

The term "disposed about" when describing positioning of the stent with respect to the graft material means that the stent is positioned within and/or over the graft material.

The term "disposed on," in connection with the below described graft materials, means that one material is incorporated (e.g., impregnated) into the holes of another material, or placed over another material or prosthesis by methods described below. For example, comminuted SIS may be disposed on at least a portion of a polymeric sheet made from porous THORALON.

In one embodiment of this invention, a graft material includes a porous polymeric sheet, ECM disposed on at least a portion of the porous polymeric sheet, and at least one polymer layer disposed on at least a portion of the ECM.

Figure 1:
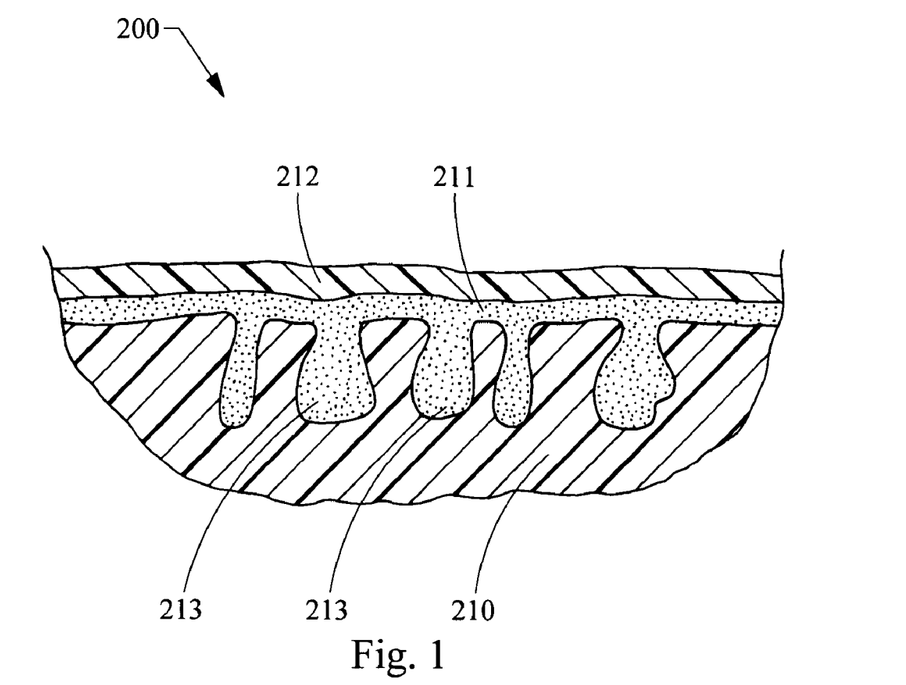
FIG. 1 shows a schematic side view illustration of one embodiment of the graft material of this invention.

FIG. 1 illustrates the graft material 200 comprising a porous polymeric sheet 210, ECM 211 disposed on at least a portion of the polymeric sheet 210, and at least one polymer layer 212 disposed on at least a portion of the ECM 211. In another embodiment, the polymer layer may be disposed on the entire ECM. Preferably, the polymeric sheet 210 comprises holes 213 and the ECM 211 is disposed or extends into the holes of the polymeric sheet. As shown in FIG. 1, the holes 213 are one-end-closed holes. As further shown in FIG. 1, the one-end-closed holes are disposed on the tissue side of the sheet 210. The polymer layer 212 may comprise THORALON.

In another embodiment of this invention, the graft material may include multiple alternate layers of porous polymeric sheets, ECM, and polymer layers, such as THORALON.

Figure 2:
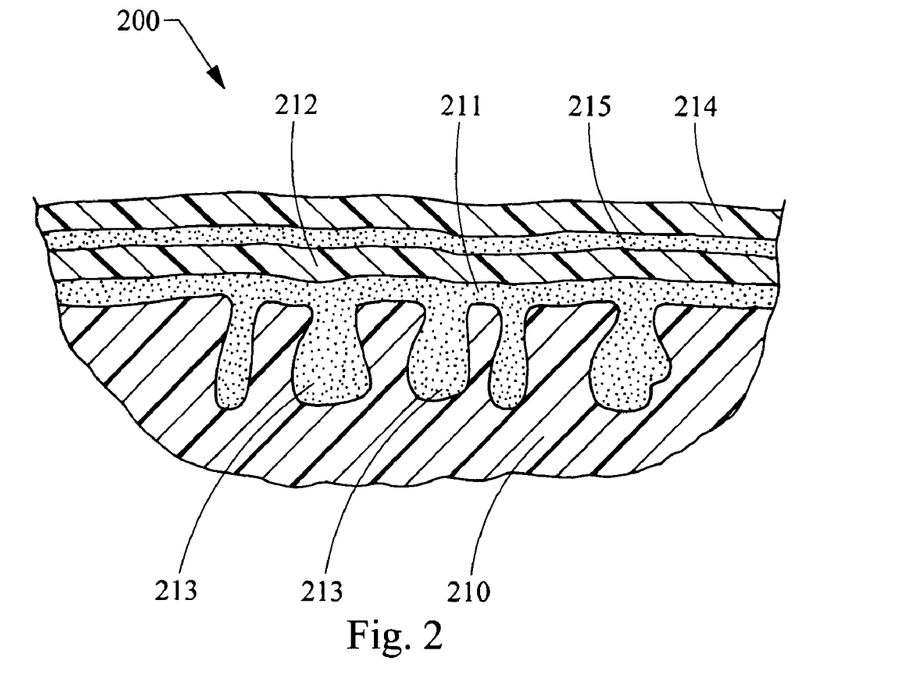
FIG. 2 shows a schematic side view illustration of another embodiment of the graft material of this invention.

FIG. 2 illustrates the graft material 200 including a polymeric sheet 210, ECM 211 disposed on at least a portion of the polymeric sheet 210, and two polymer layers 212 and 214. Preferably, the polymeric sheet 210 comprises holes 213 and the ECM 211 is disposed in the holes of the polymeric sheet. As shown in FIG. 2, the holes 213 are one-end-closed holes. As further shown in FIG. 1, the one-end-closed holes are disposed on the tissue side of the sheet 210. In one embodiment, the two polymer layers 212 and 214 comprise THORALON.

A non-metal or metal support frame (stent) may also be used, as described below.

Polymeric Sheets

Examples of suitable materials used to make porous polymeric sheets were previously described in U.S. patent application Ser. No. 11/093,759, and may include textiles or other porous polymer materials of a biocompatible material.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished by a mild, transient inflammation which typically accompanies surgery or implantation of foreign objects into a living organism.

Examples of biocompatible textile materials from which porous polymeric sheets can be formed include polyesters, such as poly(ethylene terephthalate); fluorinated polymers, such as polytetrafluoroethylene (PTFE) and fibers of expanded PTFE; and polyurethanes. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any fibrous material may be used to form a textile material for use as a polymeric sheet, provided the final polymeric sheet is biocompatible. Polymer materials that can be formed into fibers suitable for making textile porous polymeric sheets include polyethylene, polypropylene, polyamids, polyacrylonitrile, nylons and cellulose, in addition to polyesters, fluorinated polymers, and polyurethanes as listed above. Preferably the textile is made of one or more polymers that do not require treatment or modification to be biocompatible. More preferably, the textile material is made of a biocompatible polyester. Examples of biocompatible polyesters include DACRON™

(DuPont, Wilmington, Del.) and TWILLWEAVE MICREL (VASCUTEK, Renfrewshire, Scotland).

Figure 3:
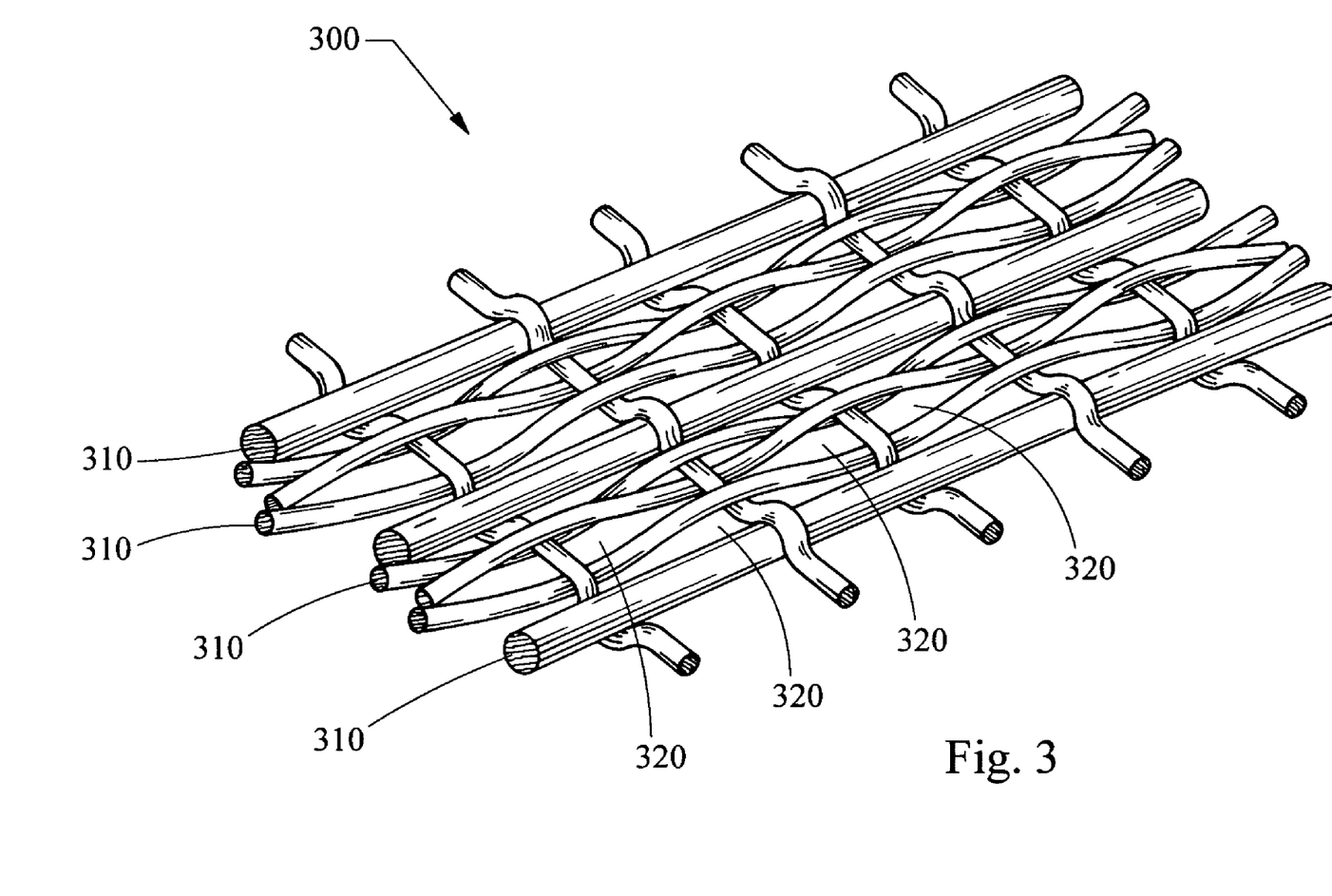
FIG. 3 is a schematic illustration of a fragmentary, perspective view of a single layer of polymeric sheet made from a woven fabric showing an exemplary distribution of filaments.

Textile materials for use as porous polymeric sheets may be woven (including knitted) textiles or nonwoven textiles. Nonwoven textiles are fibrous webs that are held together through bonding of the individual fibers or filaments. The bonding can be accomplished through thermal or chemical treatments or through mechanically entangling the fibers or filaments. Because nonwovens are not subjected to weaving or knitting, the fibers can be used in a crude form without being converted into a yarn structure. Woven textiles are fibrous webs that have been formed by knitting or weaving. The woven textile structure may be any kind of weave including, for example, a plain weave, a herringbone weave, a satin weave, or a basket weave. Referring to FIG. 3, a porous polymeric sheet 300, made from a textile material, may contain fibers 310 and interstices 320 between the fibers 310.

In one example of woven textiles, knitted textiles include weft knit and warp knit fiber arrays. Weft knit fabric structures (including double-knit structures) utilize interlocked fiber loops in a filling-wise, or weft, direction, while warp knit structures utilize fabric loops interlocked in a length wise, or warp, direction. Weft knit structures generally are more elastic than warp knit structures, but the resiliency of warp knit fabrics is satisfactory to provide a substantial degree of elasticity, or resiliency, to the fabric structure without substantially relying on tensile fiber elongation for such elasticity. Weft knit fabrics generally have two dimensional elasticity (or stretch), while warp knit fabrics generally have unidirectional (width wise) elasticity. The different elasticity properties of the various knit or woven structures may be beneficially adapted to the functional requirement of the particular graft material application. In some cases, where little elasticity is desired, the fabric may be woven to minimize in plane elasticity but yet provide flexibility. For large diameter vascular grafts (6 mm diameter or larger) and various reconstructive fabric applications, polyethylene terephthalate fiber fabric arrays of suitably small fiber size may be utilized as materials for subsequent impregnation with the extracellular collagen matrix. Commercially available woven and knitted fabrics of medical grade Dacron fibers including, single and double velour graft fabrics, stretch Dacron graft fabric and Dacron mesh fabrics, provided the fibers that have suitably small diameter and other properties to provide porous polymeric sheets in accordance with the present invention. For smaller vascular graft applications (less than 6 mm diameter), and for other applications for which suitable substrates of desired structure are not commercially available, special manufacture may be necessary.

Woven fabrics may have any desirable shape, size, form and configuration. For example, the fibers of a woven fabric may be filled or unfilled. Examples of how the basic unfilled fibers may be manufactured and purchased are indicated in U.S. Pat. No. 3,772,137, disclosure of which is incorporated by reference. Fibers similar to those described are currently being manufactured by the DuPont Company from polyethylene terephthalate (often known as "DACRON™" when manufactured by DuPont), and by other companies from various substances. Certain physical parameters may be used to characterize the textile fibers used in a graft material. The fibers may have a tensile strength of at least about 20,000 psi and a tensile modulus of at least about $2 \times 10^6$ psi. Preferably, the textile for use as a polymeric sheet is made of medical grade synthetic polymeric materials. The fibers of the textile may also have a high degree of axial orientation. The fibers may be of diameter from about 1 micron to about 5 millimeters. The denier of the textile may be from 0.5 denier per filament to 5 denier per filament. Preferably the interstices between the fibers of the textile comprise a maximum interstices spacing from about 1 micron to about 400 microns. More preferably, the interstices between the fibers of the textile comprise a maximum interstices spacing from about 1 micron to about 100 microns. Most preferably, the interstices between the fibers of the textile comprise a maximum interstices spacing from about 1 micron to about 10 microns.

Preferred textile materials for use as porous polymeric sheets include those formed from polyethylene terephthalate and PTFE. These materials are inexpensive, easy to handle, have good physical characteristics and are suitable for clinical application.

In a graft material including a polymeric sheet made from a textile material, the fibers provide a flexible array in sheet or tubular form so that the graft material may be provided with a predetermined high degree of flexibility of the graft material which also has beneficial biologically compatible properties of extracellular collagen matrix. Furthermore, a high degree of elasticity may be provided through bending of the fibers of the array rather than through substantial tensile elongation of the fibers.

Preferred textile materials for use as porous polymeric sheets are made of woven polyester having a twill weave and a porosity of about 350 ml/min/cm$^2$ (available from VASCUTEK® Ltd., Renfrewshire, Scotland, UK).

Examples of other biocompatible polymer materials from which porous polymeric sheets can be formed include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments.

In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible. More preferably, the porous sheet includes a biocompatible polyurethane.

Preferably, the porous polymeric sheet comprises a biocompatible polyurethane THORALON (THORATEC, Pleasanton, Calif.). THORALON was described in U.S. Pat. Pub. No. 2002/0065552 A1 and U.S. Pat. No. 4,675,361, both of which are incorporated herein by reference. According to these documents, THORALON is a polyurethane base polymer (referred to as BPS-215) blended with a siloxane as a surface modifying additive (referred to as SMA-300). Base polymers containing urea linkages can also be used. The concentration of the surface modifying additive may be in the range of 0.5% to 5% by weight of the base polymer.

The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference.

The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED).

THORALON can be manipulated to provide porous THORALON. Porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts. Preferably the particulate is insoluble in the solvent. The solvent may include dimethyl formamide (DMF), tetrahydrofuran (THF), dimethyacetamide (DMAC), dimethyl sulfoxide (DMSO), or mixtures thereof. The composition can contain from about 5 wt % to about 40 wt % polymer, and different levels of polymer within the range can be used to fine tune the viscosity needed for a given process. The composition can contain less than 5 wt % polymer for some spray application embodiments. The particulates can be mixed into the composition. For example, the mixing can be performed with a spinning blade mixer for about an hour under ambient pressure and in a temperature range of about 18° C. to about 27° C. The entire composition can be cast as a sheet, or coated onto an article such as a mandrel or a mold. In one example, the composition can be dried to remove the solvent, and then the dried material can be soaked in distilled water to dissolve the particulates and leave pores in the material. In another example, the composition can be coagulated in a bath of distilled water. Since the polymer is insoluble in the water, it will rapidly solidify, trapping some or all of the particulates.

The particulates can then dissolve from the polymer, leaving pores in the material. It may be desirable to use warm water for the extraction, for example water at a temperature of about 60° C. The resulting pore diameter can also be substantially equal to the diameter of the salt grains.

The porous polymeric sheet can have a void-to-volume ratio from about 0.40 to about 0.90. Preferably the void-to-volume ratio is from about 0.65 to about 0.80. The resulting void-to-volume ratio can be substantially equal to the ratio of salt volume to the volume of the polymer plus the salt.

Void-to-volume ratio is defined as the volume of the pores divided by the total volume of the polymeric layer including the volume of the pores. The void-to-volume ratio can be measured using the protocol described in AAMI (Association for the Advancement of Medical Instrumentation) VP20-1994, Cardiovascular Implants—Vascular Prosthesis section 8.2.1.2, Method for Gravimetric Determination of Porosity. The pores in the polymer can have an average pore diameter from about 1 micron to about 400 microns. Preferably the average pore diameter is from about 1 micron to about 100 microns, and more preferably is from about 1 micron to about 10 microns. The average pore diameter is measured based on images from a scanning electron microscope (SEM). Formation of porous THORALON is described, for example, in U.S. Pat. No. 6,752,826 and U.S. Pat. Pub. 2003/0149471 A1, both of which are incorporated herein by reference.

As described above, the particulate used to form the pores in the first coat may be a salt, including, but not limited to, sodium chloride (NaCl), sodium bicarbonate ($NaHCO_3$), $Na_2CO_3$, $MgCl_2$, $CaCO_3$, calcium fluoride ($CaF_2$), magnesium sulfate ($MgSO_4$), $CaCl_2$, $AgNO_3$ or any water soluble salt. However, other suspended particulate materials may be used. These include, but are not limited to, sugars, polyvinyl alcohol, cellulose, gelatin or polyvinyl pyrolidone. Preferably, the particulate is sodium chloride; more preferably, the particulate is a sugar. Preferably, the size of the particles ranges from about 5 to about 150 microns.

For example, porous THORALON foam may be created by mixing THORALON skin solution with lactose or other sugars or substances that would not denature the proteins of the ECM, such as SIS and a suitable solvent.

Other methods of creating pores in a polymeric sheet were described in U.S. Pat. No. 6,702,848 B1, disclosure of which is incorporated by reference herein.

Additionally, porous polymeric sheets may be in the form of a microporous, open-celled structure in which the pores are substantially interconnected. Microporous structures can be formed by extrusion of a mixture of polymer and one or more blowing agents. Microcellular polymeric foams can be produced by exposing the polymer to super-critical $CO_2$ under high temperature and pressure to saturate the polymer with the super-critical $CO_2$, and then cooling the polymer. Microcellular foams can be produced as described, for example, in U.S. Pat. Nos. 4,473,665 and 5,160,674, which are incorporated herein by reference. The foaming process can be carried out on extruded polymer tube by first dissolving an inert gas such as nitrogen or $CO_2$ under pressure into the polymer, and then forming microvoids by quickly decreasing the solubility of the gas in the polymer by changing the pressure or temperature, thus inducing thermodynamic instability. Examples of microporous polymeric structures are disclosed, for example, in U.S. Pat. No. 6,702,849 B1, which is incorporated herein by reference.

THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

A variety of other biocompatible polyurethanes/polycarbamates and urea linkages (hereinafter "—C(O)N or CON type polymers") may also be used as porous polymeric sheets. These include CON type polymers that preferably include a soft segment and a hard segment. The segments can be combined as copolymers or as blends. For example, CON type polymers with soft segments such as PTMO, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole.

Preferably, the hard segment is formed from a diisocyanate and diamine. The diisocyanate may be represented by the formula OCN—R—NCO, where —R— may be aliphatic, aromatic, cycloaliphatic or a mixture of aliphatic and aromatic moieties. Examples of diisocyanates include MDI, tetramethylene diisocyanate, hexamethylene diisocyanate, trimethyhexamethylene diisocyanate, tetramethylxylylene diisocyanate, 4,4'-dicyclohexylmethane diisocyanate, dimer acid diisocyanate, isophorone diisocyanate, metaxylene diisocyanate, diethylbenzene diisocyanate, decamethylene 1,10 diisocyanate, cyclohexylene 1,2-diisocyanate, 2,4-toluene diisocyanate, 2,6-toluene diisocyanate, xylene diisocyanate, m-phenylene diisocyanate, hexahydrotolylene diisocyanate (and isomers), naphthylene-1,5-diisocyanate, 1-methoxyphenyl 2,4-diisocyanate, 4,4'-biphenylene diisocyanate, 3,3'-dimethoxy-4,4'-biphenyl diisocyanate and mixtures thereof.

The diamine used as a component of the hard segment includes aliphatic amines, aromatic amines and amines containing both aliphatic and aromatic moieties. For example, diamines include ethylene diamine, propane diamines, butanediamines, hexanediamines, pentane diamines, heptane diamines, octane diamines, m-xylylene diamine, 1,4-cyclohexane diamine, 2-methypentamethylene diamine, 4,4'-methylene dianiline, and mixtures thereof. The amines may also contain oxygen and/or halogen atoms in their structures.

Other applicable biocompatible polyurethanes include those using a polyol as a component of the hard segment. Polyols may be aliphatic, aromatic, cycloaliphatic or may contain a mixture of aliphatic and aromatic moieties. For example, the polyol may be ethylene glycol, diethylene glycol, triethylene glycol, 1,4-butanediol, 1,6-hexanediol, 1,8-octanediol, propylene glycols, 2,3-butylene glycol, dipropylene glycol, dibutylene glycol, glycerol, or mixtures thereof.

Biocompatible CON type polymers modified with cationic, anionic and aliphatic side chains may also be used. See, for example, U.S. Pat. No. 5,017,664.

Other biocompatible CON type polymers include: segmented polyurethanes, such as BIOSPAN; polycarbonate urethanes, such as BIONATE; and polyetherurethanes, such as ELASTHANE; (all available from POLYMER TECHNOLOGY GROUP, Berkeley, Calif.).

Other biocompatible CON type polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Specifically, examples of siloxane-polyurethane include polymers such as ELAST-EON 2 and ELAST-EON 3 (AORTECH BIOMATERIALS, Victoria, Australia); polytetramethyleneoxide (PTMO) and polydimethylsiloxane (PDMS) polyether-based aromatic siloxane-polyurethanes such as PURSIL-10, -20, and -40 TSPU; PTMO and PDMS polyether-based aliphatic siloxane-polyurethanes such as PURSIL AL-5 and AL-10 TSPU; aliphatic, hydroxy-terminated polycarbonate and PDMS polycarbonate-based siloxane-polyurethanes such as CARBOSIL-10, -20, and -40 TSPU (all available from POLYMER TECHNOLOGY GROUP). The PURSIL, PURSIL-AL, and CARBOSIL polymers are thermoplastic elastomer urethane copolymers containing siloxane in the soft segment, and the percent siloxane in the copolymer is referred to in the grade name. For example, PURSIL-10 contains 10% siloxane. These polymers are synthesized through a multi-step bulk synthesis in which PDMS is incorporated into the polymer soft segment with PTMO (PURSIL) or an aliphatic hydroxy-terminated polycarbonate (CARBOSIL). The hard segment consists of the reaction product of an aromatic diisocyanate, MDI, with a low molecular weight glycol chain extender. In the case of PURSIL-AL the hard segment is synthesized from an aliphatic diisocyanate. The polymer chains are then terminated with a siloxane or other surface modifying end group. Siloxane-polyurethanes typically have a relatively low glass transition temperature, which provides for polymeric materials having increased flexibility relative to many conventional materials. In addition, the siloxane-polyurethane can exhibit high hydrolytic and oxidative stability, including improved resistance to environmental stress cracking. Examples of siloxane-polyurethanes are disclosed in U.S. Pat. Pub. No. 2002/0187288 A1, which is incorporated herein by reference.

In addition, any of these biocompatible CON type polymers may be end-capped with surface active end groups, such as, for example, polydimethylsiloxane, fluoropolymers, polyolefin, polyethylene oxide, or other suitable groups. See, for example the surface active end groups disclosed in U.S. Pat. No. 5,589,563, which is incorporated herein by reference.

Extracellular Matrix (ECM)

In accordance with the invention, reconstituted or naturally-derived collagenous material may be disposed on at least a portion of the porous polymeric sheet and the polymer layer is disposed on at least a portion of the material.

Reconstituted or naturally-derived collagenous materials that are at least bioresorbable will provide advantage in the present invention, with materials that are bioremodelable and promote cellular invasion and ingrowth providing particular advantage.

Suitable bioremodelable materials may be provided by collagenous extracellular matrix materials (ECMs) possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa.

As prepared, the submucosa material and any other ECM used may optionally retain growth factors or other bioactive components native to the source tissue. For example, the submucosa or other ECM may include one or more growth factors such as basic fibroblast growth factor (FGF-2), transforming growth factor beta (TGF-beta), epidermal growth factor (EGF), and/or platelet derived growth factor (PDGF). As well, submucosa or other ECM used in the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression.

Submucosa or other ECM materials may be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with specific staining. Such non-collagenous solids can constitute a significant percentage of the dry weight of the ECM material in certain inventive embodiments, for example at least about 1%, at least about 3%, and at least about 5% by weight in various embodiments of the invention.

The submucosa or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the infiltration of new blood vessels. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7,833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of native bioactive components, non-native bioactive components such as those synthetically produced by recombinant technology or other methods, may be incorporated into the submucosa or other ECM tissue. These non-native bioactive components may be naturally-derived or recombinantly produced proteins that correspond to those natively occurring in the ECM tissue, but perhaps of a different species (e.g. human proteins applied to collagenous ECMs from other animals, such as pigs). The non-native bioactive components may also be drug substances. Illustrative drug substances that may be incorporated into and/or onto the ECM materials used in the invention include, for example, antibiotics or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after engraftment of the material in the patient.

Submucosa or other ECM tissue used in the invention is preferably highly purified, for example, as described in U.S. Pat. No. 6,206,931, disclosure of which is incorporated herein in its entirety. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of the submucosa tissue used in the present invention.

Small intestine submucosa (hereinafter "SIS") is one preferred form of ECM. SIS may be harvested and delaminated in accordance with the description in U.S. Pat. Nos. 4,956,178 and 4,902,508. SIS may be a preferred material because it has special bio-remodeling characteristics. Commercially available SIS material is derived from porcine small intestinal submucosa that remodels to the qualities of its host when implanted in human soft tissues. SIS is commercially available from Cook Biotech, West Lafayette, Ind.

Purified ECM may be further processed in a number of ways to provide ECM suitable for disposing on the polymeric sheet.

One way is to prepare a comminuted form of ECM. The comminuted forms of ECM may be prepared without loss of the source tissue's ability to induce the growth of endogenous tissues. Comminuted ECM compositions are prepared as solutions or suspensions or powder of ECM and comprise mechanically obtained ECM or enzymatically treated ECM. In one example, the ECM may be mechanically and enzymatically treated to form a substantially uniform or homogenous solution. In another example, the ECM may be treated with a protease, such as trypsin or pepsin, or other appropriate enzymes for a period of time sufficient to solubilize the tissue and form a substantially homogeneous solution.

Preferably, the ECM starting material is mechanically comminuted by tearing, cutting, grinding, shearing and the like. Grinding the ECM in a frozen or freeze-dried state is preferred although good results can be obtained as well by subjecting a suspension of pieces of the ECM to treatment in a high speed (high shear) blender and dewatering, if necessary, by centrifuging and decanting excess water. The resultant fluidized ECM may be dried to form ECM powder. Thereafter, it can be hydrated, that is, combined with water or buffered saline and optionally other pharmaceutically acceptable excipients to form ECM composition as a fluid having a viscosity of about 2 to about 300,000 cps at 25° C. The higher viscosity ECM compositions may have a gel or paste consistency. The fluidized compositions may be sterilized using art-recognized sterilization techniques such as exposure to ionizing radiation. The preparation of fluidized forms of, for example, intestine submucosa is described in U.S. Pat. Nos. 5,275,826, 5,516,533, and 6,264,992, the disclosures of which are incorporated herein by reference in their entirety.

The powder form of ECM may be prepared by pulverizing ECM source tissue under liquid nitrogen to produce particles ranging in size from 0.01 to 1 mm in their largest dimension. The particulate composition may then be lyophilized overnight, pulverized again and optionally sterilized to form a substantially anhydrous particulate composite. Alternatively, the powder form of ECM may be formed from fluidized ECM by drying.

Variations of the above-described processing procedures may be used to produce ECM material that may be disposed on a porous polymeric sheet.

The purified ECM may be conditioned, as described in U.S. patent application Ser. No. 08/916,490, disclosure of which is incorporated by reference in its entirety, to alter the viscoelastic properties of the purified ECM. The purified ECM may be conditioned by, for example, stretching, chemically treating, enzymatically treating or exposing the matrix structure to other environmental factors.

ECM prepared using any variation of the processes described above, may be selectively disposed on at least a portion of a polymeric sheet prior to disposing a polymer layer on the ECM and forming a graft material, as described below.

It is desirable that the ECM be substantially free of any antibiotics, antiviral agents or any antimicrobial agents which may affect the inherent biochemical profile of the matrix and its efficacy upon implantation. One method of treating ECM material includes rinsing the delaminated tissue in saline and soaking it in an antimicrobial agent, for example, as disclosed in U.S. Pat. No. 4,956,178, which is incorporated herein by reference. However, preferred processes avoid the use of antimicrobial agents and the like, which may affect the biochemical profile of the matrix and/or be unnecessarily introduced into the patient.

Polymer Layer

As described, the graft material includes a porous polymeric sheet and ECM disposed on at least a portion of the polymeric sheet. The graft material further includes one or more polymer layers disposed on at least a portion of the ECM. Preferably, the polymer layer comprises any polymer that may be porous or non-porous, provided it is biocompatible. Non-porous polymers are preferred as a polymer layer. Some examples of suitable polymers that may be used as a polymer layer include polyolefins, polyacrylonitrile, nylons, polyaramids and polysulfones, polyesters, fluorinated polymers, polysiloxanes, polyurethanes, and other polymers as listed above in connection with the porous polymeric sheet. Preferably, the polymer layer includes a biocompatible polyurethane THORALON, which may be either porous or non-porous and may be in the form of skin film, skin fibers, porous foam, or a combination of these.

Porous THORALON was described above.

Non-porous THORALON can be formed, for example, by mixing the polyetherurethane urea (BPS-215) and the surface modifying additive (SMA-300) in a solvent, such as dimethyl formamide (DMF), tetrahydrofuran (THF), dimethyacetamide (DMAC), dimethyl sulfoxide (DMSO). The composition can contain from about 5 wt % to about 40 wt % polymer, and different levels of polymer within the range can be used to fine tune the viscosity needed for a given process. The composition can contain less than 5 wt % polymer for some spray application embodiments. The entire composition can be cast as a sheet, or coated onto an article such as a mandrel or a mold. In one example, the composition can be dried to remove the solvent.

Preferably, THORALON is used as a polymer layer because of its relatively lower thrombogenicity as compared to other polyurethanes that do not contain SMA-300. Other polyurethanes with equivalent properties to THORALON, however, may also be used as the polymer layer and are preferred.

This polymer layer may serve as a bioinductive layer to promote ingrowth and proliferation of endothelial and other existing cells located on or in the blood vessel wall and/or in the blood stream. Also, the polymer layer may serve to improve the lubricity of the graft.

Preparation of the Graft Material

The graft material may be prepared by providing a porous polymeric sheet, ECM, and at least one polymer layer. The porous polymeric sheet comprises holes and the ECM is disposed in the holes of the polymeric sheet. The ECM remains disposed on the polymeric sheet until after implantation. The ECM may be disposed on the porous polymeric sheet by coating, lining and/or impregnating the polymeric sheet with the ECM. The coating, lining and/or impregnation may be provided to reduce the porosity of the porous polymeric sheet at the time of implantation, thus avoiding or reducing blood loss through a porous graft. Such an ECM treatment can also contribute to the biocompatibility of the prosthesis material. Preferably, the porous polymeric sheet comprises holes and the ECM is disposed in the holes of the polymeric sheet, for example, by impregnation.

The term "impregnation" means providing for the presence of one or more components inside the polymeric sheet structure, in particular in the holes, such as interstices or pores of the polymeric sheet structure. Preferably, at least a substantial portion of the holes are open holes prior to treatment with ECM. More preferably at least the majority of the total hole volume is provided by open holes. Open holes extend from one surface of the graft material to another. Preferably at least a portion of the holes are filled with extracellular collagen matrix, such as comminuted intestine submucosa. The impregnation may partially or fully fill the holes. Preferably the impregnation is provided as a layer at least partially covering the inner surface of the holes, while maintaining a sufficient openness (porosity) to allow migration of cells or precursors thereof into the graft material. The graft material may be impregnated with the ECM in a fluidized form or in a powder form. The ECM may be applied to the polymeric sheet directly at a desired location or may be pre-applied before application to the patient.

In one example, the ECM containing solution is disposed on at least a portion of the polymeric sheet in any manner capable of uniformly impregnating the sheet. Fluidized ECM may be added to the polymeric sheet after preparation of the sheet, for example by soaking, dipping, spraying, painting, or otherwise applying the ECM to the sheet. Dipping and spraying are two conventional methods for impregnating the solution although dipping is preferred. In this method, the polymeric sheet may be dipped into a bath containing the fluidized ECM. The impregnated graft material is then removed from the bath and allowed to dry. During the drying step, the solvent evaporates leaving the ECM on the polymeric sheet of the graft material. The extent to which the fluidized ECM is impregnated into the polymeric sheet of the graft material is selected depending on the desired absorption capabilities of the graft material. Generally, the greater the amount of the ECM impregnated, the greater the absorption capability of the graft material and the longer the graft material may be retained at the desired location on a patient's body.

Preferred methods of applying fluidized ECM to a polymeric sheet may include, for example vacuum impregnation and impregnation under pressure, which were described in U.S. Pat. No. 5,037,377, disclosure of which is incorporated by reference in its entirety. In one example of the vacuum impregnation process, the tubular polymeric sheets, which are highly porous in their unimpregnated form, are plugged at one end and are filled with fluidized ECM. The sheets are kept in a vessel which is evacuated to obtain a pressure differential in the physiological pressure range, preferably approximately 120 millimeters of mercury (mmHg). The pressure differential forces the fluidized ECM to flow through the holes of the polymeric sheet. Thereafter, the graft is incubated at 37 degrees centigrade, as noted above. Typically, the step of incubation is conducted in such a manner that the actual temperature of the graft material is maintained at 37 degrees centigrade for approximately twenty minutes. Thereafter, the polymeric sheet, including ECM, may be dried for approximately twenty minutes. The steps of vacuum impregnation, incubation, and drying are repeated until tests with saline under physiological pressure (typically 120 Hgmm) show the polymeric sheet, including the ECM, to be sufficiently impervious to liquid. Usually, the steps of vacuum impregnation, incubation, and drying must be repeated approximately two to four times (most typically three times) to obtain substantially liquid impervious polymeric sheet, including the ECM.

In one example of the process of impregnation under pressure, the tubular polymeric sheets may be plugged at one end. Thereafter, fluidized ECM is placed under physiological pressure (usually 120 mmHg) into the tubular sheets. The pressure causes the fluidized ECM to flow through the polymeric sheet of the graft. After pressurization, the graft materials are incubated and dried as described in connection with the vacuum impregnation process. The process of impregnation under pressure, incubation, and drying is repeated until tests show that the graft is substantially impervious to liquid under physiological pressure. Usually, the procedure must be repeated two to four, most often three, times.

Another exemplary method of impregnating a porous polymeric sheet with an ECM includes mixing the comminuted ECM with the components of the sheet in a solvent prior to forming the sheet. In the example of THORALON, the polyetherurethane urea and siloxane-containing surface modifying additive can be mixed with comminuted ECM in a solvent. If the ECM is fluidized, it is preferable that the solvent not dissolve the ECM. A sheet can be formed by casting the mixture and evaporating the solvent. A sheet can also be formed by coagulating the mixture in a liquid that is a non-solvent for the polyetherurethane urea, the siloxane-containing surface modifying additive and the ECM. The sheet forming procedure can be optimized to insure that ECM is present in the holes of the polyetherurethane urea. This method may also be used to form a coating of a porous polymers containing ECM in the holes on an existing medical device.

When the ECM impregnated grafts are sufficiently impervious to liquid, they may be immersed in a solution of glutaraldehyde for cross-linking and for deprivation of the antigenicity properties of the foreign animal proteins. In one example, treatment with 0.35 percent (by weight) or like concentration aqueous glutaraldehyde solution of approximately 7.4 pH is used to cross-link the ECM fibers with one another. Treatment with glutaraldehyde links the collagenous ECM fibers to one another, because it causes covalent chemical bond bridges to form between several protein chains of the fibers. The graft materials of the invention may then be stored and transported in glutaraldehyde or saline solution.

The ECM may also be disposed on the porous polymeric sheet by binding it through photo-linking or other available means. Photo-linking, photo-activation, photo-polymerization, photo-crosslinking or photo-coupling refers to a process that is activated by light. A photo-activated step can be used to link the extracellular collagen matrix to a polymeric sheet to form graft materials of this invention. The photo-activation step may require the presence of a photoinitiator, examples of which include acetophenones, benzophenones, hydroxipropiophenones, thioxanthones, diphenyl ketones, benzoin and benzoin alkyl ethers, halogen substituted alkylaryl ketones, or quinone and anthraquinone derivatives.

The ECM may also be immobilized by allowing interaction between the ECM and the polymeric sheet under conditions where a stable covalent or non-covalent linkage forms, e.g., by photo-crosslinking the ECM if it and the surface comprise photo-activatable groups. "Stable" in this context refers to a linkage that is not disrupted during use of the fluidized ECM in a subsequent procedure, e.g., under washing or binding conditions. After immobilization, the surface can then be soaked, for example, in an aqueous buffer to remove non-covalently attached ECM and excess cross-linking components and/or reagents.

Once the ECM is disposed on the porous polymeric sheet of the graft material, the sheet may be dried before being worked or used. This may be done by freeze-drying, convection drying, or by microwave or other heating. This will leave the dry ECM in the holes of the polymeric sheet, which can then be worked to make the final product (which can be stored in dry form). Just before use, the graft material may be wetted with the appropriate liquid (water or buffered saline) to restore the ECM to its liquid form and make it readily diffusible out of the sheet. The product also can be used dry where it will be adequately wetted after application (due to the wetness of the site of use).

Following the ECM application, one or more polymer layers are disposed on at least a portion of the ECM of the graft material. Alternatively, the polymer layer is disposed on the entire ECM. Preferably, the polymer is biocompatible polyurethane, such as THORALON. The polymer layer may be disposed on the ECM using any technique known in the art, including coating, dipping and spraying. In a preferred embodiment, the biocompatible polymer layer may be applied as a solution. To do so, the polymer may be substantially dissolved in a solvent or combination of solvents, where the solvent may be defined as any fluid capable of placing the polymer substantially into solution at a desired concentration. One specific example of a suitable solvent may be dimethyl acetamide (DMAC) for use with polyurethane. If necessary, gentle heating and/or agitation, such as stirring, may be employed to cause substantial dissolution.

In one embodiment, THORALON foam may be created, as described above, for disposing on the ECM. For example, the foam may be created by mixing THORALON skin solution with lactose or other sugars and a solvent into a solution. This solution may then be disposed on at least a portion of the ECM. Following the deposition of the solution, the graft material may be immersed in water until the sugars are dissolved out of the polymer layer. Once the graft material is formed, the solvent present in the polymer layer may be removed by air drying at room temperature or oven drying at an elevated temperature. Alternatively, vacuum drying may be performed. In this case, the ECM may become lyophilized. The ECM may be re-hydrated following implantation into a patient's body.

In a preferred embodiment, the liquid polymer for the polymer layer is selected such that it is the same as the polymeric sheet forming the graft material. For example, in a more preferred embodiment, the liquid polymer is THORALON and the polymeric sheet of the graft material includes porous THORALON.

In another embodiment, the polymer layer may be applied by electrostatic spinning, or "electrospinning." Electrospinning is a process for creating fine polymer fibers using an electrically charged solution that is driven from a source to a target with an electrical field. Using an electric field to draw the positively charged solution results in a jet of solution from the orifice of the source container to the grounded target. The jet forms a cone shape, called a Taylor cone, as it travels from the orifice. Typically, as the distance from the orifice increases, the cone becomes stretched until, near the target, the jet splits or splays into many fibers prior to reaching the target. Also prior to reaching the target, and depending on many variables, including target distance, charge, solution viscosity, temperature, solvent volatility, polymer flow rate, and others, the fibers begin to dry. These fibers are extremely thin, typically measured in nanometers. The collection of these fibers on the target, assuming the solution is controlled to ensure the fibers are still wet enough to adhere to each other when reaching the target, form a randomly-oriented fibrous material with extremely high porosity and surface area, and a very small average pore size. A detailed discussion of electrospinning is disclosed in U.S. Pat. Pub. No. 2004/0051201, which is incorporated by reference herein in its entirety.

By manipulating appropriate variables, the electrospun fibers achieve characteristics that allow them to form a fabric that can adhere to an object, such as a graft, so that the object becomes covered; or the fibers can be used to create a free-standing polymer "skin" that has a variety of applications.

The ECM may be covered with the fibrous polymer layer by providing a spinneret charged with an electric potential relative to a predetermined location on a target plate. The graft is placed between the spinneret and the predetermined location on said target plate. A liquid polymer or a polymer solution, generated by either heating the polymer until it achieves a plastic state or mixing the polymer with a solvent to form a solution, is then forced through the spinneret, thereby transferring at least some of the electric potential to the polymer such that the polymer forms a stream directed toward the target plate due to the electric potential between the liquid and the plate. Before it reaches the plate, the stream splays into a plurality of nanofibers due to the electric potential between the liquid and the plate. At least some, preferably most, of the nanofibers collide with the graft material instead of reaching the target plate. The predetermined location on the target plate is then moved relative to the object until the entire object is covered. This is accomplished by moving the needle, electronically moving the point on the target plate where the potential is greatest relative to the needle, moving the object itself, or a combination of these three techniques.

Alternatively, the stent may be coated electrostatically by making the stent the target instead of placing it in front of the target. Also, the stent may be coated by placing the stent on the metal mandrel and use the mandrel and the mandrel as the target. The stent is rotated to effect an even distribution of fibers.

In another embodiment, the polymer layer may be applied by electrospraying. Methods of coating medical devices by electrospraying were previously described in U.S. Pub. No. 2003/143315, which is incorporated by reference herein in it entirety.

In one embodiment, multiple alternate layers of polymeric sheet, ECM, and polymer layers may be used. For example, the graft material may include a polymeric sheet and ECM disposed on at least a portion of the polymeric sheet. The graft material may further include a polymer layer, a second layer of ECM, and a second polymer layer, the ECM being placed between the two polymer layers.

Preferably, graft materials of this invention are treated with antibiotics to prevent infection and to encourage healing, and may be used for certain kinds of prostheses, such as vascular grafts. An artificial graft may be filled with an antibiotic to prevent post-operation infections around the surgical field, with steroids to prevent rejection of the graft material, and with antimetabolites to prevent excessive scar formation around the graft. Furthermore, steroids may be augmented with VEGF, certain prostaglandins, carbon nanotubes, L-arginine or other substances that may encourage endothelialization on the inner lumen wall of graft material. Likewise they may be filled with heparin, an anticoagulant, to prevent excessive clotting around the prosthesis.

The graft materials described herein may be used, for example, for treatment of damaged or diseased tissues on a patient's body. The graft materials, upon placement on the damaged or diseased tissue on a patient's body, may serve as a rapidly vascularized matrix for support and growth of new endogenous tissue. The graft material may be then remodeled (resorbed and replaced with autogenous differentiated tissue) and can assume the characterizing features of the tissue with which the graft material is associated at the site of placement.

In one example, the graft materials can be used in a method for promoting healing of tissues. For example, damaged or diseased portions of the patient's body may be repaired by placing a patch of the graft material. In another example, the graft material may be used to create bioresorbable wound dressings or band-aids. Wound dressings may be used as a wound-healing dressing, a tissue sealant (i.e., sealing a tissue or organ to prevent exposure to a fluid or gas, such as blood, urine, air, etc., from or into a tissue or organ), and/or a cell-growth scaffold. Such a wound dressing may protect the injured tissue and maintain a moist environment, and may be water permeable, easy to apply, non-toxic, non-antigenic, not require frequent changes and maintain microbial control.

Bioresorbable sealants and adhesives may be used in combination with the graft materials. Examples of bioresorbable sealants and adhesives include FOCALSEAL® (biodegradable eosin-PEG-lactide hydrogel requiring photopolymerization with Xenon light wand) produced by Focal; BERIPLAST® produced by Adventis-Bering; VIVOSTAT® produced by ConvaTec (Bristol-Meyers-Squibb); SEALAGEN™ produced by Baxter; FIBRX® (containing virally inactivated human fibrinogen and inhibited-human thrombin) produced by CyoLife; TISSEEL® (fibrin glue composed of plasma derivatives from the last stages in the natural coagulation pathway where soluble fibrinogen is converted into a solid fibrin) and TISSUCOL® produced by Baxter; QUIXIL® (Biological Active Component and Thrombin) produced by Omrix Biopharm; a PEG-collagen conjugate produced by Cohesion (Collagen); HYSTOACRYL® BLUE (ENBUCRILATE) (cyanoacrylate) produced by Davis & Geck; NEXACRYL™ (N-butyl cyanoacrylate), NEXABOND™, NEXABOND™ S/C, and TRAUMASEAL™ (product based on cyanoacrylate) produced by Closure Medical (TriPoint Medical); DERMABOND™ which consists of 2-Octyl Cyanoacrylate produced by Dermabond (Ethicon); TISSUEGLU® produced by Medi-West Pharma; and VETBOND™ which consists of n-butyl cyanoacrylate produced by 3M.

Wound dressings may be used for soft tissue repair, including nerve repair, organ repair, skin repair, vascular repair, muscle repair, and ophthalmic applications. In other examples, wound dressings may be used to treat a surface such as, for example, a surface of the dermis and epidermis, the site of an anastomosis, a suture, a staple, a puncture, an incision, a laceration, or an apposition of tissue.

Wound dressings may be used in association with any medical condition that requires coating or sealing of a tissue. For example, bodily fluids may be stopped or minimized; barriers may be applied to prevent post-surgical adhesions, including those of the pelvis and abdomen, pericardium, spinal cord and dura, tendon and tendon sheath. Wound dressings may also be useful for treating exposed skin, in the repair or healing of incisions, abrasions, burns, inflammation, and other conditions requiring application of a coating to the outer surfaces of the body. Preferably, the graft material of this invention is used for wound healing and introduction of endogenous connective tissue in a patient in need of such treatment.

In a preferred embodiment, the graft materials, including a porous polymeric sheet, ECM and at least one polymer layer, may be used to manufacture medical devices, such as endoprostheses. Desirably, these medical devices are vascular or endovascular devices, such as grafts, stents and combination stent-grafts. However, other medical devices may also be manufactured using the graft material of this invention.

The functional vessels of human and animal bodies, such as blood vessels and ducts, occasionally weaken or even rupture. For example, in the aortic artery, the vascular wall can weaken or tear, resulting in dangerous conditions such as aneurysm and dissection. Treatment of such conditions can be performed by implanting a prosthesis within the vascular system using minimally invasive surgical procedures. An endoluminal prosthesis typically includes one or more stents affixed to graft material and is delivered to the treatment site by endovascular insertion. Once the endoluminal prosthesis is radially enlarged, it should remain in place indefinitely by self-attachment to the vessel wall, acting as a substitute vessel for the flow of blood or other fluids.

In one embodiment of this invention, an endoluminal prosthesis includes a tubular graft comprising a polymeric sheet, ECM, disposed on at least a portion of the polymeric sheet, and at least one polymer layer disposed on at least a portion of the ECM. Preferably, the polymer layer is disposed on the external, i.e. the tissue side of the graft material. Alternatively, the polymer layers may be applied to the internal, i.e., lumen side of the graft material. In one embodiment, it may be preferable to apply polymer layers to both, the internal and the external sides of the graft material. The endoluminal prosthesis also includes a stent disposed about the graft material. The stent may be a self-expanding stent or a balloon expandable stent. The endoluminal prosthesis may also include a plurality of stents.

Figure 4:
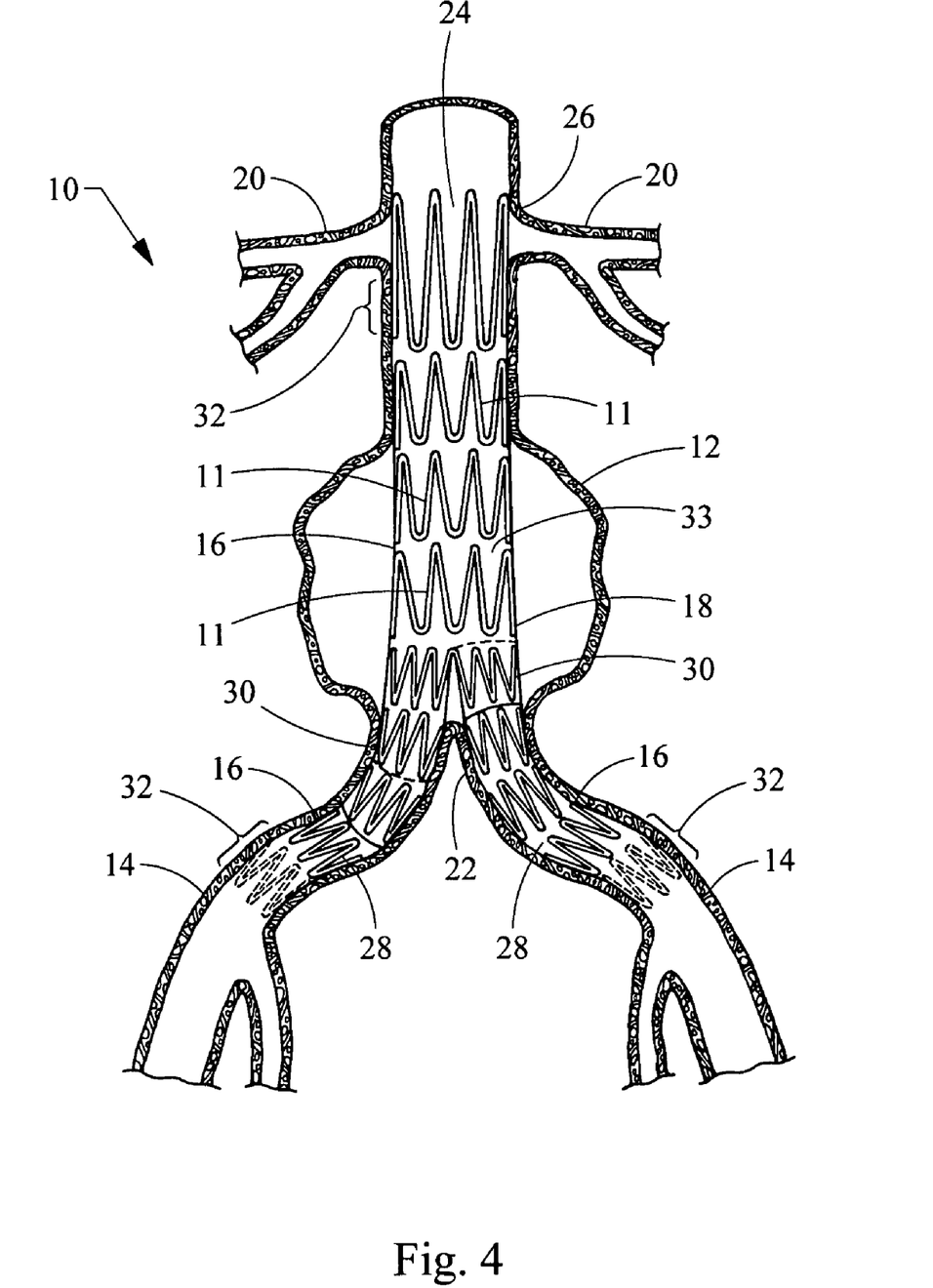
FIG. 4 shows a stent graft impregnated with extracellular collagen matrix.

FIG. 4 shows an example of a modular bifurcated stent graft 10 deployed within an aneurysmal aorta 12 and both iliac arteries 14. Comminuted ECM is impregnated into the polymeric sheet 33. The prosthetic modules 16 that make up the stent graft 10 are generally tubular, so that the fluid can flow through the stent graft 10, and are preferably made of biocompatible polyurethane, polysiloxane, polyester, fluorinated polymer; or a textile, such as poly(ethylene terephthalate) or similar materials. The main body 18 extends from the renal arteries 20 to near the bifurcation 22. Multiple Z-stents 11 are sutured along the length of the stent graft 10. A suprarenal fixation stent 24 anchors the main body 18 to the healthier, preferably non-aneurysmal tissue 26 near the renal arteries. Two iliac extension modules 28 extend from the iliac limbs 30.

The stent graft 10 will preferably achieve a blood-tight seal at the contact regions 32 on both ends of the aneurysm 12, so that the aneurysm 12 will be excluded. Usually, the contact regions 32 contain, for example Z-stents on the inside of the stent graft 10. Alternatively, or in addition, other elements, such as rings, may also be included in the contact regions 32. In the particular embodiment shown in FIG. 4, the stent graft 10 contacts the vascular tissue below the renal arteries 20, around the bifurcation 22 and at the iliac limbs 30 and extensions 28. In this embodiment, a seal is preferably achieved that will help exclude the entire aneurysmal region and, as a result, the hemodynamic pressures within the aneurysm 12 may be reduced. These seals may be improved by the addition of extracellular collagen matrix to the polymeric sheet of the stent.

Figure 5:
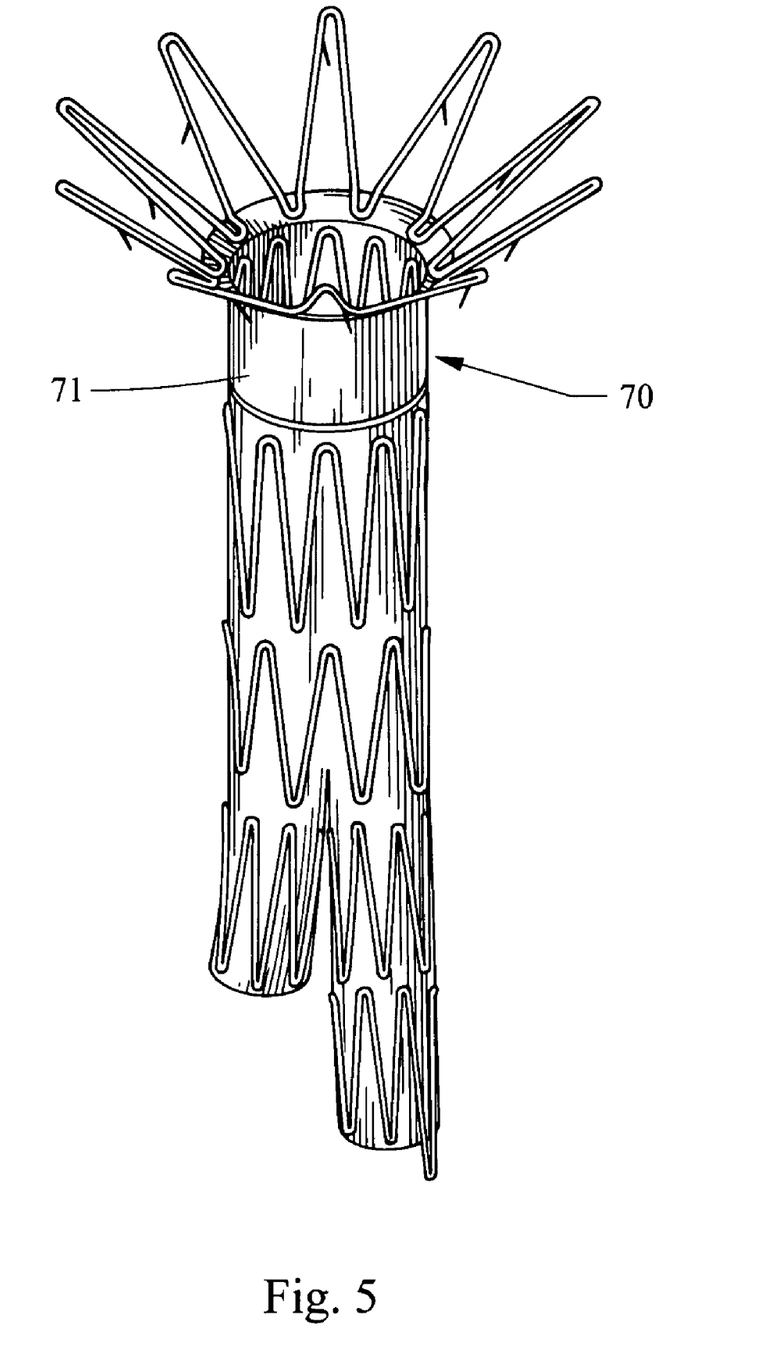
FIG. 5 shows an aorto-uniiliac endoluminal prosthesis with polymeric material impregnated with an extracellular collagen matrix material.

FIG. 5 shows a modular aorto-uniiliac stent graft 70 similar to that described in U.S. patent application Ser. No. 10/104,672, which is incorporated herein by reference. The polymeric sheet 71 has extracellular collagen matrix incorporated into the interstices of the textile 71. The use of ECM can improve the seal and prevent migration of the graft 70.

In one example, only a portion of a polymeric sheet used as a graft material for an endoluminal device comprises ECM, such as comminuted intestine submucosa disposed in holes of the polymeric sheet, forming ECM bands. These ECM bands are preferably positioned at or near appropriate targets for fixation and/or encouraging circumferential apposition to the surrounding vessel. These bands may further include a polymer layer disposed on the ECM. Examples of various devices that include ECM bands, were described in U.S. patent application Ser. No. 11/094,021, U.S. patent application Ser. No. 10/644,129; U.S. Provisional Application Ser. No. 60/404,662; and U.S. Provisional Application Ser. No. 60/572,806, which are incorporated by reference.

Other uses of the graft material of this invention will be apparent to those of ordinary skill in the art. The contents of all references, patents and published applications cited throughout this application are hereby incorporated by reference herein.

It is to be understood that this invention is not limited to the particular methodology, protocols, animal species or genera, constructs, or reagents described and as such may vary. It is also to be understood that the terminology used herein is for the purpose of describing particular embodiments only, and is not intended to limit the scope of the present invention which will be limited only by the appended claims. It is therefore intended that the foregoing detailed description be regarded as illustrative rather than limiting, and that it be understood that it is the following claims, including all equivalents, that are intended to define the spirit and scope of this invention.

The invention claimed is:

1. A graft material, comprising:
   a polymeric sheet having a tissue side, the tissue side having at least one one-end-closed hole;
   a bioremodelable extracellular matrix material (ECM) disposed on at least a portion of the tissue side of the polymeric sheet and extending into the at least one one-end-closed hole of the polymeric sheet, and
   at least one polymer layer disposed on at least a portion of the ECM,
   wherein the polymeric sheet and the at least one polymer layer both comprise a polyetherurethane urea and a surface modifying agent,
   wherein the ECM is processed from a source tissue to retain one or more growth factors native to the source tissue and to provide biotropic properties, and
   wherein the polymeric sheet, the at least one polymer layer, and the ECM are distinct and separate layers.

2. The graft material of claim 1, wherein the polymer layer is disposed on the entire ECM.

3. The graft material of claim 1, wherein the surface modifying agent is siloxane.

4. The graft material of claim 1, wherein the polymeric sheet is in the form of a foam.

5. The graft material of claims 1, wherein the ECM is small intestine submucosa.

6. The graft material of claim 5, wherein the small intestine submucosa is comminuted.

7. The graft material of claim 5, wherein the small intestine submucosa is in a gel form.

8. The graft material of claim 1, wherein the polymeric sheet has disposed thereon one or more pairs of a further ECM layer and a further polymer layer.

9. The graft material of claim 1, further comprising a porous polymeric sheet disposed on at least a portion of the polymeric sheet.

10. An endoluminal prosthesis, comprising:
    a tubular graft material comprising
    a polymeric sheet having a tissue side and at least one one-end-closed hole only on the tissue side of the polymeric sheet,
    a bioremodelable extracellular matrix material (ECM) disposed on at least a portion of the tissue side of the polymeric sheet and extending into the at least one one-end-closed hole of the polymeric sheet,
    at least one polymer layer disposed on at least a portion of the ECM, and
    a stent disposed about the graft material;
    wherein the polymeric sheet and the at least one polymer layer both comprise a polyetherurethane urea and a surface modifying agent;
    wherein the ECM is processed from a source tissue to retain one or more growth factors native to the source tissue and to provide biotropic properties, and
    wherein the polymeric sheet, the at least one polymer layer, and the ECM are distinct and separate layers.

11. The prosthesis of claim 10, wherein the stent is a self-expanding stent or a balloon expandable stent.

12. The prosthesis of claim 10, wherein the ECM is small intestine submucosa.

13. The prosthesis of claim 10, wherein the surface modifying agent is siloxane.

14. The prosthesis of claim 10, wherein the polymer layer is disposed on the entire ECM.

15. The endoluminal prosthesis of claim 10, further comprising a porous polymeric sheet disposed on at least a portion of the polymeric sheet.

16. A method of making a graft for implantation, comprising:
- providing a polymeric sheet having a tissue side, the tissue side having at least one one-end-closed hole, the polymeric sheet comprising a polyetherurethane urea and a surface modifying agent;
- providing a bioremodelable extracellular matrix material (ECM);
- disposing ECM on at least a portion of the tissue side of the polymeric sheet so that the ECM extends into the at least one one-end-closed hole of the polymeric sheet, and
- disposing at least one layer of a polymer material comprising a polyetherurethane urea and a surface modifying agent on at least a portion of the ECM;
- wherein the ECM remains disposed on the polymeric sheet until after implantation;
- wherein the ECM is processed from a source tissue to retain one or more growth factors native to the source tissue and to provide biotropic properties;
- wherein the at least one one-end-closed hole is disposed only on the tissue side of the graft; and
- wherein the polymeric sheet, the at least one polymer layer, and the ECM are distinct and separate layers.

17. The method of claim 16, further comprising disposing a porous polymeric sheet on at least a portion of the at least one layer of the polymer material.

18. The method of claim 17, further comprising disposing another layer of ECM on at least a portion of the porous polymeric sheet.

19. The method of claim 16, further comprising disposing a porous polymeric sheet on at least a portion of the polymeric sheet.

* * * * *